(12) United States Patent
Cheng et al.

(10) Patent No.: US 9,827,340 B2
(45) Date of Patent: Nov. 28, 2017

(54) MOBILE UV STERILIZATION DEVICE AND METHOD

(71) Applicant: Maxim Integrated Products, Inc., San Jose, CA (US)

(72) Inventors: Jim Chih-Min Cheng, Fremont, CA (US); Cheng-Wei Pei, Belmont, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 0 days.

(21) Appl. No.: 14/745,760

(22) Filed: Jun. 22, 2015

(65) Prior Publication Data

US 2016/0184467 A1 Jun. 30, 2016

Related U.S. Application Data

(66) Substitute for application No. 62/096,592, filed on Dec. 24, 2014.

(51) Int. Cl.
*A61L 2/10* (2006.01)
*C02F 1/32* (2006.01)
*C02F 1/00* (2006.01)

(52) U.S. Cl.
CPC .............. *A61L 2/10* (2013.01); *C02F 1/325* (2013.01); *C02F 1/002* (2013.01);
(Continued)

(58) Field of Classification Search
CPC .. A61L 2/10; C02F 1/325; C02F 1/002; C02F 2201/3222; C02F 2303/04;
(Continued)

(56) References Cited

U.S. PATENT DOCUMENTS 4,779,130 A * 10/1988 Yabe ...................... A61B 1/05
348/76
6,468,433 B1* 10/2002 Tribelski ............... A01M 1/226
205/435
(Continued)

FOREIGN PATENT DOCUMENTS

IN WO 2011021228 A2 * 2/2011 ............. C02F 1/325
JP 2002238846 A * 8/2002 ............. A61B 1/06

OTHER PUBLICATIONS

English translation of JP 2002238846, Aug. 27, 2002.*

*Primary Examiner* — Regina M Yoo
(74) *Attorney, Agent, or Firm* — Advent, LLP (57) ABSTRACT

A mobile sterilization assembly, a mobile sterilization device, and method for sterilization using a mobile sterilization device are described for providing a low-cost and compact sterilization system using an ultraviolet light-emitting diode for sterilization. In an implementation, a mobile sterilization assembly includes a sterilization assembly couplable to a mobile device with a controller, the sterilization assembly including at least one light dispersive element; and an optical coupler configured to couple the at least one light dispersive element to a mobile device; where the at least one light dispersive element at least one of transmits and disperses light from at least one light-emitting diode or transmits light to a photodiode, where the at least one light-emitting diode or the photodiode are configured to be communicatively coupled to the controller.

27 Claims, 4 Drawing Sheets

(52) U.S. Cl.
CPC ..... *C02F 2201/326* (2013.01); *C02F 2201/3222* (2013.01); *C02F 2201/3224* (2013.01); *C02F 2201/3228* (2013.01); *C02F 2209/006* (2013.01); *C02F 2209/008* (2013.01); *C02F 2303/04* (2013.01)

(58) Field of Classification Search
CPC ........ C02F 2201/3228; C02F 2201/326; C02F 2209/006; C02F 2209/008; C02F 2201/3224
See application file for complete search history.

(56) References Cited

U.S. PATENT DOCUMENTS

| | | | | |
|---|---|---|---|---|
| 7,182,147 B2 * | 2/2007 | Cutler | ................... | B25B 21/00 173/1 |
| 7,922,650 B2 * | 4/2011 | McWeeney | ........ | A61B 1/00071 600/104 |
| 8,109,981 B2 * | 2/2012 | Gertner | ................. | A61N 5/0603 606/13 |
| 2004/0204151 A1 * | 10/2004 | Muthuswamy | ..... | H04M 1/7253 455/567 |
| 2007/0019398 A1 * | 1/2007 | Chen | ....................... | B60Q 7/00 362/102 |
| 2008/0185314 A1 * | 8/2008 | Tomasello | ............. | A61B 18/24 206/570 |
| 2011/0286883 A1 * | 11/2011 | Hecht | ....................... | A23L 3/28 422/24 |
| 2012/0321509 A1 * | 12/2012 | Bak | ........................... | A61L 2/10 422/24 |
| 2013/0048877 A1 * | 2/2013 | Thoren | ................... | G02B 6/102 250/492.1 |
| 2014/0341777 A1 * | 11/2014 | Deshays | ................... | A61L 2/24 422/24 |
| 2015/0220766 A1 * | 8/2015 | Russell | ............. | G06K 7/10881 235/462.42 |
| 2015/0305610 A1 * | 10/2015 | Giraldo Cadavid | ..... | A61B 1/05 600/560 |

* cited by examiner

MOBILE UV STERILIZATION DEVICE AND METHOD

CROSS-REFERENCE TO RELATED APPLICATIONS

The present application claims the benefit under 35 U.S.C. §119(e) of U.S. Provisional Application Ser. No. 62/096,592, filed Dec. 24, 2014, and titled "MOBILE UV STERILIZATION DEVICE AND METHOD." U.S. Provisional Application Ser. No. 62/096,592 is herein incorporated by reference in its entirety.

BACKGROUND

Ultraviolet germicidal irradiation (UVGI) is a method for disinfection that utilizes ultraviolet (UV) light to kill microorganisms. UV light includes electromagnetic radiation with wavelengths shorter than visible light. UVGI utilizes short-wavelength ultraviolet radiation (UV-C) that is harmful to microorganisms. It can be effective in destroying the nucleic acids in these organisms such that their DNA is disrupted by the UV radiation, leaving them unable to perform vital cellular functions.

SUMMARY

A mobile sterilization assembly, mobile sterilization device, and method for sterilization using a mobile sterilization device are described for providing a low-cost and compact sterilization system using an ultraviolet light-emitting diode for sterilization. In one implementation, a mobile sterilization assembly includes a sterilization assembly couplable to a mobile device with a controller, the sterilization assembly including at least one light dispersive element; and an optical coupler configured to couple the at least one light dispersive element to a mobile device; where the at least one light dispersive element at least one of transmits and disperses light from at least one light-emitting diode or transmits light to a photodiode, where the at least one light-emitting diode or the photodiode are configured to be communicatively coupled to the controller.

In an implementation, a mobile sterilization device includes a mobile device with a controller; and a sterilization assembly couplable to the mobile device, the sterilization assembly including at least one light dispersive element; and an optical coupler configured to couple the at least one light dispersive element to a mobile device; where the at least one light dispersive element at least one of transmits and disperses light from at least one light-emitting diode or transmits light to a photodiode, where the at least one light-emitting diode or the photodiode are configured to be communicatively coupled to the controller.

In an implementation, a method for sterilization using a mobile sterilization device includes activating a light-emitting diode for obtaining an index of refraction for a material; receiving an indication of the index of refraction of the material using a photodiode; determining an indication of a safety threshold using the index of refraction; and activating an ultraviolet light emitting diode when the safety threshold is indicated, where the light-emitting diode, the photodiode, and the ultraviolet light emitting diode are included in a mobile sterilization device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Overview

Current sterilization methods often use fluorescent bulbs for short-wavelength ultraviolet radiation (UVC) for water purification and sterilization in large appliances (e.g., air filtration, waste water treatment plants) as well as smaller devices (e.g., a sterilizing pen or water bottle). Systems and devices using fluorescent bulbs may be offered for outdoor applications and as specialized devices with high costs. However, these systems and devices may not be readily available or affordable, especially within geographical areas having the greatest need. Additionally, the fluorescent bulbs can limit the size of the sterilization device and can require device cleaning each time after usage for contaminated dirt and/or water from the sterilizing surface. Some alternatives to using a fluorescent sterilization bulb include chemical tablets (which can affect taste of the water or require cleaning of the surface following usage), current fluorescent bulb-based systems (which are bulkier and have limited integration into portable devices often carried with consumers, such as a mobile phone), and boiling of the water, which may require a large amount of power and may be limited as a portable solution, especially when time is considered. Other methods, such as short-wave ultraviolet light-emitting diode sterilization technology, have yet to be adopted largely due to cost of the package and/or power issues when compared to fluorescent bulbs.

Accordingly, a mobile sterilization assembly, a mobile sterilization device, and a method for sterilization using a mobile sterilization device are described that provide a low-cost, compact sterilization system using an ultraviolet light-emitting diode for sterilization. In one implementations, a mobile sterilization assembly includes a sterilization assembly couplable to a mobile device with a controller, the sterilization assembly including at least one light dispersive element; and an optical coupler configured to couple the at least one light dispersive element to a mobile device; where the at least one light dispersive element at least one of transmits and disperses light from at least one light-emitting diode or transmits light to a photodiode, where the at least one light-emitting diode or the photodiode are configured to be communicatively coupled to the controller.

In one implementation, a mobile sterilization device includes a mobile device with a controller; and a sterilization assembly couplable to the mobile device, the sterilization assembly including at least one light dispersive element; and an optical coupler configured to couple the at least one light dispersive element to a mobile device; where the at least one light dispersive element at least one of transmits and disperses light from at least one light-emitting diode or transmits light to a photodiode, where the at least one light-emitting diode or the photodiode are configured to be communicatively coupled to the controller.

In an implementation, a method for sterilization using a mobile sterilization device includes activating a light-emitting diode for obtaining an index of refraction for a material; receiving an indication of the index of refraction of the material using a photodiode; determining an indication of a safety threshold using the index of refraction; and activating an ultraviolet light emitting diode when the safety threshold is indicated, where the light-emitting diode, the photodiode, and the ultraviolet light emitting diode are included in a mobile sterilization device.

The mobile sterilization assembly and mobile sterilization device can use an ultraviolet light-emitting diode (e.g., a UVC LED) and/or another color LED (e.g., red, blue) bundled with a mobile device with an attachable sterilization assembly. When used with a liquid, the color LED may be used to check an index of refraction of the liquid to determine whether the light dispersive element is immersed. The UVC LED can then be activated for illumination and sterilization. In some embodiments, the mobile sterilization assembly may be used to sterilize a volume of liquid and/or a surface. A portable UVC LED and a sterilization assembly can provide upfront sterility and better volume coverage while limiting the power necessary to provide sterilization.

Example Implementations

Figure 1:
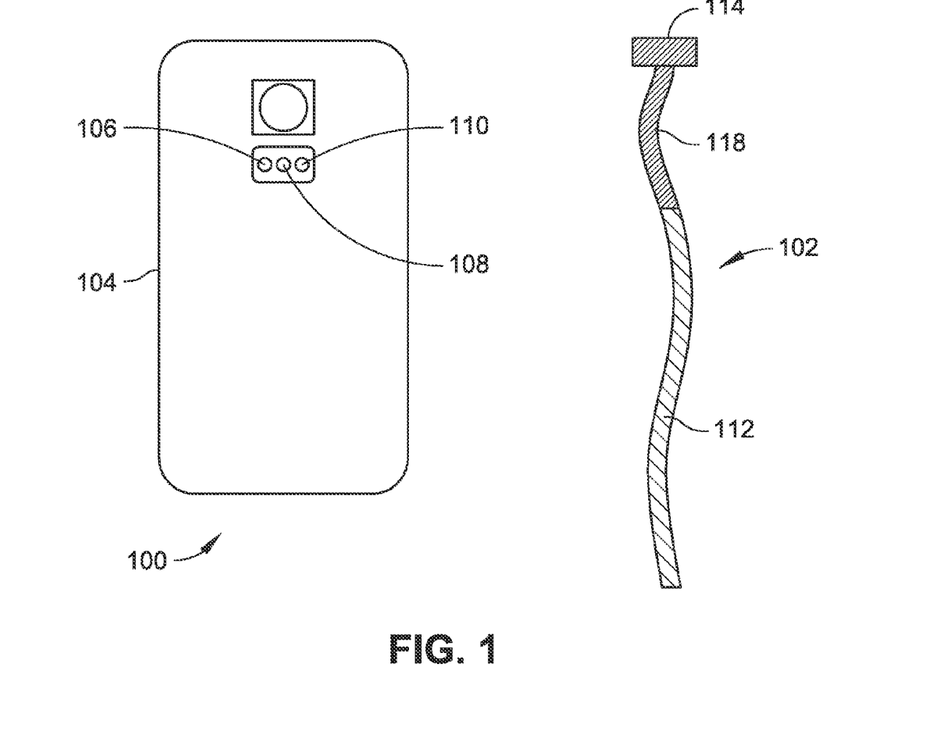
FIG. 1 is a diagrammatic view illustrating a mobile sterilization device including a mobile device and a light dispersive element, in accordance with an example implementation of the present disclosure.

FIGS. 1 through 4 and 6 illustrate a mobile sterilization device 100 in accordance with an example implementation of the present disclosure. FIG. 1 illustrates the mobile sterilization device 100 including a sterilization assembly 102, and a mobile device 104. In implementations, the sterilization assembly 102 can include a light dispersive element 112 and an optical coupler 114. The sterilization assembly 102 can be configured to be disposable and low-cost providing for a more accessible and affordable sterilization device.

As illustrated in FIGS. 1 through 4, the sterilization assembly 102 can include at least one light dispersive element 112. In some embodiments, a light dispersive element 112 can include an optical fiber configured to function as a waveguide and transmit light between two points and/or ends of the fiber. Additionally, the light dispersive element 112 can diffuse and/or disperse light from the surface(s) of the light dispersive element 112 (e.g., through the ends or other sides of a fiber). The light dispersive element 112 may include a flexible, transparent fiber formed from a silica, polymer, and/or composite material. In a specific example, the light dispersive element 112 includes a fused silica material. In another specific example, the light dispersive element 112 includes a polymer material. The light dispersive element 112 can include a light-diffusing fiber configured to diffuse light from a light-emitting diode 108 and/or an ultraviolet light-emitting diode 106. In a specific embodiment, the light dispersive element 112 can diffuse light from a light-emitting diode 108 into and/or onto a material (e.g., water, a table surface, etc.) and can be configured to transmit refracted and/or reflected light (originating from the light-emitting diode 108) from the material to a photodiode 110 in order to determine an index of refraction of the material. In this specific embodiment, the light dispersive element 112 can subsequently further diffuse ultraviolet light from an ultraviolet light-emitting diode 106 into and/or onto the material. Diffusing the ultraviolet light into and/or onto the material can serve to sterilize the material. In a specific example, the sterilization assembly 102 includes a first light dispersive element 112 that determines a liquid's refractive index using a light-emitting diode 108 and includes a second light dispersive element 112 for transmitting ultraviolet light from an ultraviolet light-emitting diode to sterilize the liquid. In another specific embodiment, the sterilization assembly 102 includes a single light dispersive element that is optically coupled to the ultraviolet light-emitting diode 106 and the light-emitting diode 108 and can transmit light from the light-emitting diode 108 and ultraviolet light from the ultraviolet light-emitting diode 106.

The light dispersive element 112 can include varying lengths, diameters, and forms. In some implementations, the light dispersive element 112 can include a cylindrical element having a diameter from about 100 µm to a centimeter or more. Additionally, the light dispersive element 112 can include lengths from about a centimeter to several meters in length. In one specific embodiment, a light dispersive element 112 can be about 500 µm in diameter and about 20 cm in length. In another specific embodiment, the light dispersive element 112 can be about 125 µm in diameter and about 10 cm in length. It is contemplated that the light dispersive element 112 can include other sizes, shapes, and/or forms. For example, the light dispersive element 112 may include a long, thin sheet (which can be flexible) and may include a diffuser on at least one side.

Figure 2:
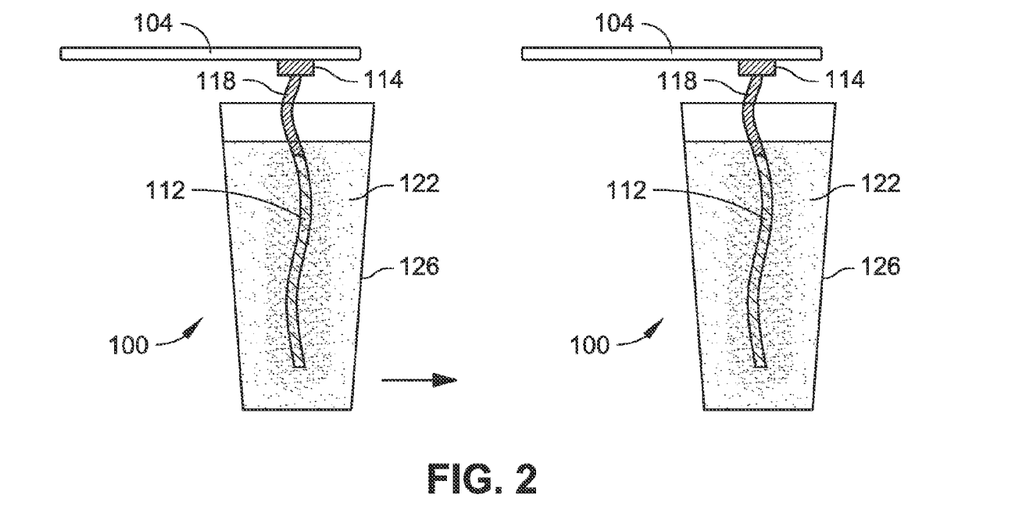
FIG. 2 is a diagrammatic view illustrating the mobile sterilization device in FIG. 1 sterilizing a liquid, where the mobile sterilization device includes a mobile device and a light dispersive element, in accordance with an example implementation of the present disclosure.

As shown in FIGS. 1 and 2, the light dispersive element 112 can include cladding 118. Cladding 118 can include at least one layer of material with a lower refractive index than the light dispersive element 112 and can surround at least a portion of the light dispersive element 112. In the portion of the light dispersive element 112 with cladding 118, the cladding 118 can cause light transmitted through the light dispersive element 112 to be confined to the core of the light dispersive element 112 due to internal reflection of the transmitted light by the cladding 118 at the boundary of the cladding 118 and the light dispersive element 112. In implementations, the cladding 118 can be formed from materials such as ultra-pure glass and/or a polymer. In a specific example, a light dispersive element 112 includes a cladding 118 formed from a polymer that is configured to block and/or reflect ultraviolet light, where the cladding 118 is disposed on the light dispersive element 112 about 10% of the length of the light dispersive element 112. In this specific example, the cladding is disposed proximate to an end of the light dispersive element 112 including an optical coupler 114. In some embodiments, the light dispersive element 112 may include a clear outer jacket, buffer coating, or covering. In a specific embodiment, the light dispersive element 112 may include a 500 µm diameter clear polyvinyl chloride outer jacket.

As shown in FIGS. 1 through 4, the sterilization assembly 102 can include an optical coupler 114. The optical coupler 114 can include an optical fiber connector or other coupler configured to couple and/or attach the light dispersive element 112 to a device (e.g., a mobile device 104) external to the sterilization assembly 102. The optical coupler 114 can serve to terminate an end of the light dispersive element 112 while facilitating the transmittal of light from the mobile device 104 or other external device to the light dispersive element 112 and enable quick connection and/or disconnection from the mobile device 104. The optical coupler 114 can be configured to mechanically couple and align the light dispersive element 112 core so that light can pass to and/or from a light receiver (e.g., photodiode 110) and/or a light source (e.g., light-emitting diode 108, ultraviolet light-emitting diode 106), respectively. The optical coupler 114 can include at least one connector with varying coupling mechanisms, for example, a magnet (e.g., a self-aligned magnetic assembly), a mechanical clamp, a snap, a screw, a push-pull connector, a clip, and/or a bayonet-type connector. In one specific example, an optical coupler 114 can include a straight tip (ST) connector. In another specific embodiment, the optical coupler 114 can include a magnetic assembly for coupling the sterilization assembly 102 to the mobile device 104. In this specific embodiment, the magnetic assembly may include at least one magnet, which may be self-aligning, and the mobile device 104 and/or external device may also include at least one magnet. In a specific embodiment, the optical coupler 114 may include at least one of a light-emitting diode 108, an ultraviolet light-emitting diode 106, and/or a photodiode 110. In this embodiment, the optical coupler 114 can include a power source assembly configured to provide power and/or receive power from a power source (e.g., a battery, a mobile device 104) and/or communications assembly (e.g., wiring, wireless capability such as Bluetooth) configured to communicate with a controller 124. In implementations, the sterilization assembly 102 and/or the mobile device 104 can include a power source 136, such as a battery and/or an energy scavenging circuit. In these implementations, the power source 136 can serve to provide sufficient energy for operating the sterilization assembly 102 and/or mobile sterilization device 100. In a specific example, at least one of the photodiode 110, the ultraviolet light-emitting diode 106, the controller 124, or the power source 136 may be disposed as a portion of the sterilization assembly 102.

In some implementations, the sterilization assembly 102 may include an ultraviolet shield 116. In one embodiment, the ultraviolet shield 116 can include foil or a metalized plastic shield configured to reflect, shield, and/or block ultraviolet light. For example, the ultraviolet shield 116 can be disposed between a light dispersive element 112 and a mobile device 104. Using an ultraviolet shield 116 may provide a configuration for sterilization of a hard surface (e.g., a table top, a counter, etc.). In this example, the sterilization assembly 102 including the light dispersive element 112 and the ultraviolet shield 118 can be disposed parallel to an associated mobile device 104. Ultraviolet light can be transmitted through the light dispersive element 112 and diffused into surrounding ambient air and onto a surface to sterilize the surface and/or air while ultraviolet light is blocked from the mobile device 104. Additionally, other configurations may be used, such as a wand-like application where the UV may then be used, for example, for illumination of a fluorescent body (e.g., a bio-labs separation gel), or for the general consumer, sterilization of a countertop or table at a fast-food restaurant.

Figure 3:
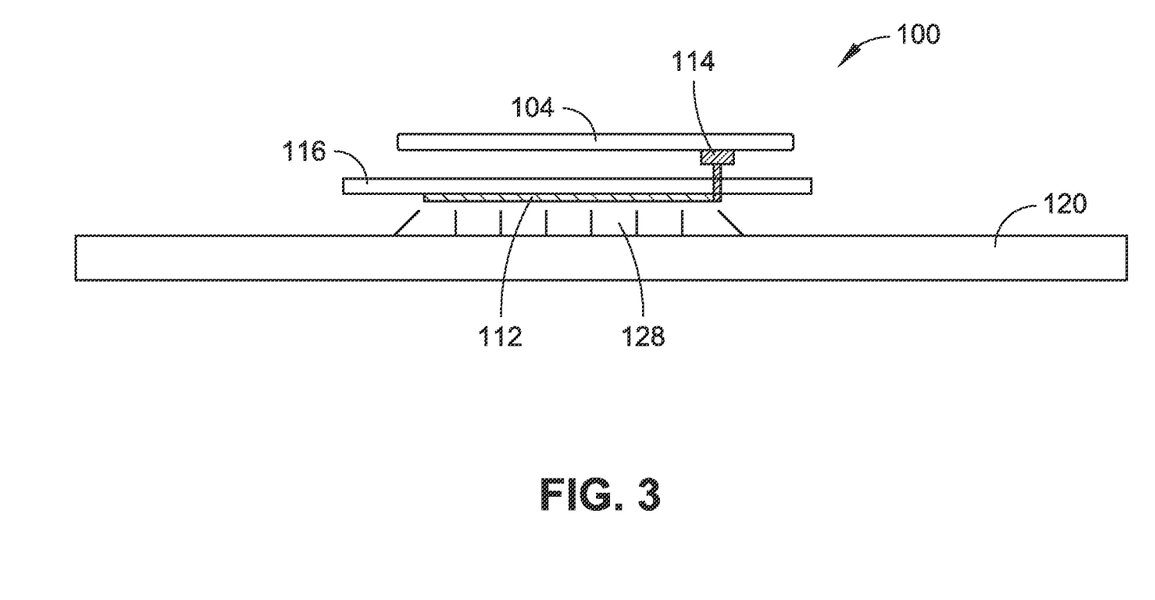
FIG. 3 is a diagrammatic view illustrating the mobile sterilization device in FIG. 1 sterilizing a surface, where the mobile sterilization device includes a mobile device and a light dispersive element with an ultraviolet shield, in accordance with an example implementation of the present disclosure.
Figure 4:
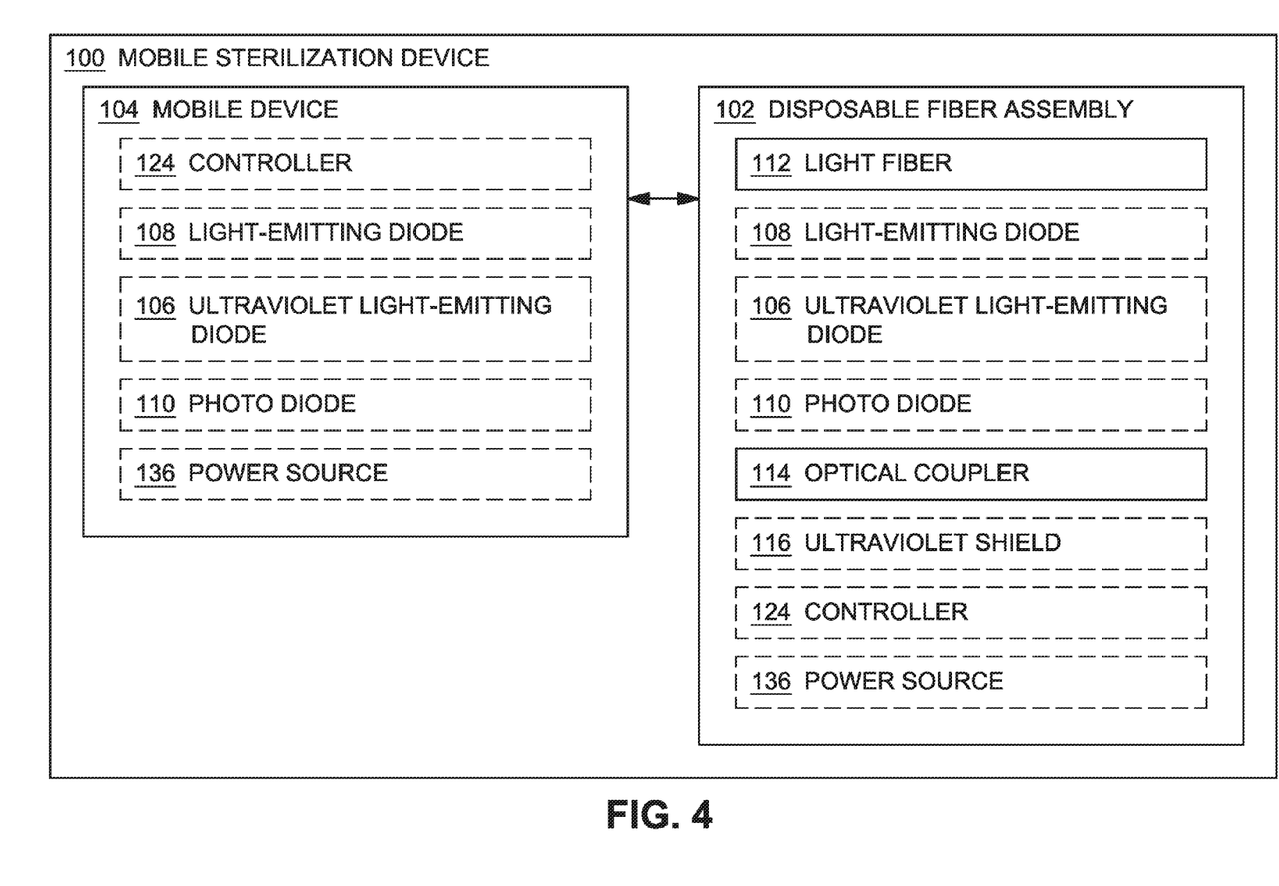
FIG. 4 is an environmental view illustrating the mobile sterilization device in FIG. 1, where the mobile sterilization device includes a mobile device and a sterilization assembly with a light dispersive element, in accordance with an example implementation of the present disclosure.

As shown in FIGS. 1, 3, and 4, the mobile sterilization device 100 can include a mobile device 104. A mobile device 104 can include a wide variety of small, hand-held computing devices. In some implementations, a mobile device 104 may include a display screen with a touch input and/or a miniature keyboard that generally weighs less than 2 pounds. Some examples of a mobile device 104 can include, for example, a smartphone, a tablet computer, and/or a wearable device (e.g., a watch, clothing including computing capability). In one specific embodiment, the mobile device 104 includes a smartphone.

In some implementations, the mobile device 104 may include at least one of a light-emitting diode 108 (LED), an ultraviolet light-emitting diode 106 (UVC LED), and/or a photodiode 110. In some implementations, the sterilization assembly 102 may include a light-emitting diode 108, an ultraviolet light-emitting diode 106, and/or a photodiode 110. A light-emitting diode 108 may include a two-lead semiconductor light source and may include a basic pn-junction diode, which emits light when activated. The light-emitting diode 108 can be activated by a controller 124 and configured to transmit light through a light dispersive element 112, which light can then be dispersed to and/or reflected/refracted from a material (e.g., water, air, etc.) in order to determine an index of refraction.

An ultraviolet light-emitting diode 106 can include a specific light-emitting diode that is configured to emit ultraviolet (UV) light at a sufficiently short wavelength, which can be effective at destroying microorganisms. In one specific instance, the ultraviolet light-emitting diode 106 can include a short-wave ultraviolet light-emitting diode. In other instances, the ultraviolet light-emitting diode 106 may include other light wavelengths. For example, the mobile device and/or the sterilization assembly 102 may include two or more ultraviolet light-emitting diode 106, where the two or more ultraviolet light-emitting diodes 106 can emit ultraviolet light with the same wavelengths or may emit ultraviolet light with differing wavelengths. The ultraviolet light-emitting diode 106 can transmit light through the light dispersive element 112, which is subsequently diffused into the material (e.g., water, air, etc.) through the side(s) or end(s) of the light dispersive element 112.

The photodiode 110 can include a semiconductor device that converts light into electrical current. The electrical current can be generated when photons are absorbed in the photodiode 110. For instance, the photodiode 110 can be configured to receive and/or detect light originated from light-emitting diode 108, transmitted through and diffused by the light dispersive element 112, reflected/refracted by a material (e.g., air, water), and transmitted back through the light dispersive element 112 to the photodiode 110, resulting in a specific electrical current. The resulting electrical current can be measured and/or correlated with a specific index of refraction using a controller 124.

In a specific embodiment illustrated by FIG. 2, a mobile sterilization device 100 includes a mobile device 104 and a sterilization assembly 102. In this specific embodiment, the mobile sterilization device 100 can be used to sterilize a liquid 122 (e.g., water) in a container 126. Shown in FIG. 2, a sterilization assembly 102 and light dispersive element 112 can be immersed in the liquid 122. The light-emitting diode 108 can then be activated, and light from the light-emitting diode 108 can be transmitted and diffused into the liquid 122 via the light dispersive element 112 (shown on the left side of FIG. 2). The diffused light can be reflected back through the light dispersive element 112 to the photodiode 110, which can detect the reflected light and create a corresponding electrical current. A controller 124 can then determine from the corresponding electrical current whether a predetermined safety threshold and/or safety parameter has been met (e.g., whether the index of refraction indicates a liquid, a non-liquid, a specific type of liquid, etc.). In the embodiment illustrated by FIG. 2, the index of refraction can indicate that the light dispersive element 112 is immersed in a liquid 122, and the controller 124 can then activate the ultraviolet light-emitting diode 106, which can transmit ultraviolet light through the light dispersive element 112, which can further diffuse the ultraviolet light into the liquid 122 and effectively sterilize the liquid 122, as illustrated on the right side of FIG. 2.

In a specific embodiment illustrated by FIG. 3, the mobile sterilization device 100 can be used to sterilize a surface 120 and/or an object. As shown in FIG. 3, a sterilization assembly 102 includes an ultraviolet shield 116 and a light dispersive element 112. The light-emitting diode 108 can be activated using a controller 124, and light from the light-emitting diode 108 can be transmitted and diffused into ambient air 128 via the light dispersive element 112. The diffused light can be reflected back through the light dispersive element 112 to the photodiode 110, which can receive and/or detect the reflected light and create a corresponding electrical current indicating a specific material index of refraction (e.g., air). A controller 124 can then determine from the corresponding electrical current whether a predetermined safety threshold and/or safety parameter has been met (e.g., whether the index of refraction indicates air). In the embodiment illustrated by FIG. 3, the index of refraction can indicate that the light dispersive element 112 is immersed in air 128, and the controller 124 can then activate the ultraviolet light-emitting diode 106, which can transmit ultraviolet light through the light dispersive element 112, which ultraviolet light is further diffused into the ambient air 128 and onto the surface 120, effectively sterilizing the surface 120. As can further be seen in FIG. 3, the diffused ultraviolet light may be reflected and/or directed by the ultraviolet shield 116 to a specific surface or area (e.g., a portion of a table top, etc.). The ultraviolet shield 116 can function to protect the mobile device 104 and/or a user from ultraviolet light and can direct the ultraviolet light to an object and/or material to be sterilized.

As shown in FIG. 4, the mobile device 104 can include a controller 124 configured to control and operate the sterilization process of the mobile sterilization device 100, the mobile device 104, and/or the sterilization assembly 102. In embodiments, the controller 124 can be disposed in the mobile device 104 and/or electrically coupled to the ultraviolet light-emitting diode 106, the light-emitting diode 108, and/or the photodiode 110. In another embodiment, the controller 124 can be disposed as a part of the sterilization assembly 102 wherein the sterilization assembly 102 can perform its own onboard calculations. In one specific embodiment, a sterilization assembly 102 can include a controller 124 that can calculate ultraviolet exposure time and intensity for sterilizing a specific sample. In this specific embodiment, the calculation by controller 124 may depend on sensed environmental factors, such as material clarity and/or amount.

Figure 6:
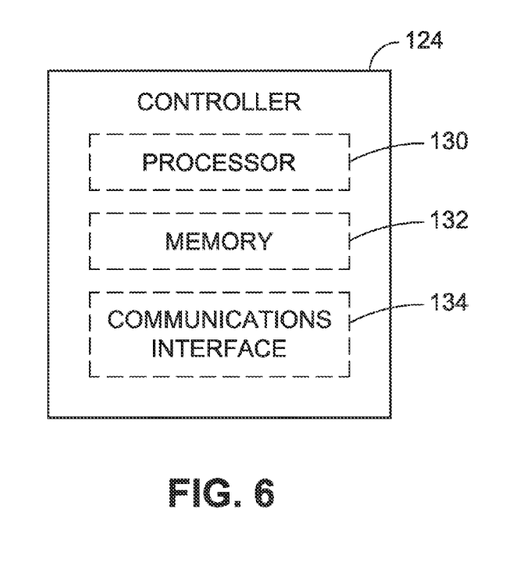
FIG. 6 is an environmental view illustrating a controller included in the mobile sterilization device in FIG. 1, in accordance with an example implementation of the present disclosure.

Illustrated in FIGS. 4 and 6, a mobile sterilization device 100, including some or all of its components, can operate under computer control. For example, a processor 130 can be included with or in a mobile sterilization device 100 and/or controller 124 to control the components and functions of mobile sterilization device 100 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the mobile sterilization device 100. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

The light-emitting diode 108, the ultraviolet light-emitting diode 106, and/or the photodiode 110 can be coupled with a controller 124 for controlling the mobile sterilization device 100. The controller 124 can include a processor 130, a memory 132, and a communications interface 134. The processor 130 provides processing functionality for the mobile sterilization device 100/controller 124 and can include any number of processors, micro-controllers, or other processing systems, and resident or external memory for storing data and other information accessed or generated by the mobile sterilization device 100/controller 124. The processor 130 can execute one or more software programs that implement techniques described herein. The processor 130 is not limited by the materials from which it is formed or the processing mechanisms employed therein and, as such, can be implemented via semiconductor(s) and/or transistors (e.g., using electronic integrated circuit (IC) components), and so forth.

The controller 124 may include a memory 132. The memory 132 can be an example of tangible, computer-readable storage medium that provides storage functionality to store various data associated with operation of the mobile sterilization device 100/controller 124, such as software programs and/or code segments, or other data to instruct the processor 130, and possibly other components of the mobile sterilization device 100/controller 124, to perform the functionality described herein. Thus, the memory 132 can store data, such as a program of instructions for operating the mobile sterilization device 100 (including its components), and so forth. It should be noted that while a single memory 132 is described, a wide variety of types and combinations of memory (e.g., tangible, non-transitory memory) can be employed. The memory 132 can be integral with the processor 130, can comprise stand-alone memory, or can be a combination of both.

The memory 132 can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the mobile sterilization device 100 and/or the memory 132 can include removable integrated circuit card (ICC) memory, such as memory provided by a subscriber identity module (SIM)

card, a universal subscriber identity module (USIM) card, a universal integrated circuit card (UICC), and so on.

The controller 124 may include a communications interface 154. The communications interface 134 can be operatively configured to communicate with components of the mobile sterilization device 100. For example, the communications interface 134 can be configured to transmit data for storage in the mobile sterilization device 100, retrieve data from storage in the mobile sterilization device 100, and so forth. The communications interface 134 can also be communicatively coupled with the processor 130 to facilitate data transfer between components of the mobile sterilization device 100 and the processor 130 (e.g., for communicating inputs to the processor 130 received from a device communicatively coupled with the mobile sterilization device 100/controller 124). It should be noted that while the communications interface 134 is described as a component of a mobile sterilization device 100/controller 124, one or more components of the communications interface 134 can be implemented as external components communicatively coupled to the mobile sterilization device 100 via a wired and/or wireless connection. The mobile sterilization device 100 can also comprise and/or connect to one or more input/output (I/O) devices (e.g., via the communications interface 134), including, but not necessarily limited to: a display, a mouse, a touchpad, a keyboard, and so on.

The communications interface 134 and/or the processor 130 can be configured to communicate with a variety of different networks, including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface 134 can be configured to communicate with a single network or multiple networks across different access points.

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system, or circuit. Further, elements of the blocks, systems, or circuits may be implemented across multiple integrated circuits. Such integrated circuits may comprise various integrated circuits, including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block, or circuit may be implemented using its software or firmware equivalent. In other instances, one part of a given system, block, or circuit may be implemented in software or firmware, while other parts are implemented in hardware.

Example Fabrication Processes

Figure 5:
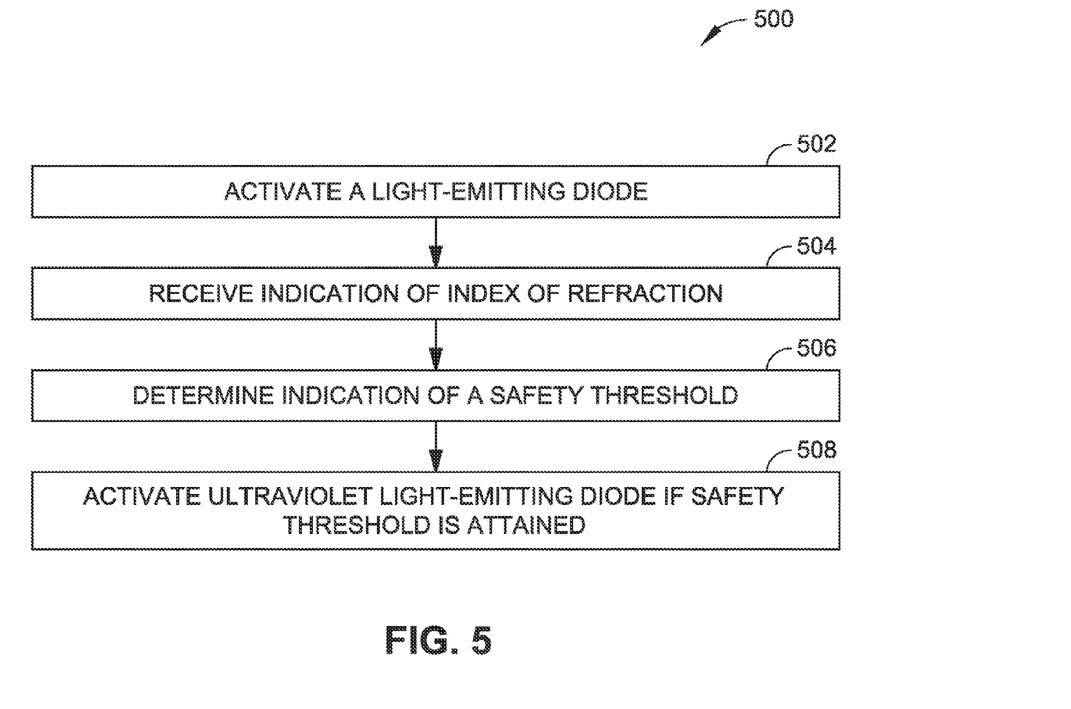
FIG. 5 is a flow diagram illustrating a process in an example implementation for sterilization of a material using a mobile sterilization device, such as the mobile sterilization device shown in FIG. 1.

The following discussion describes example techniques for operating a mobile sterilization device, such as the mobile sterilization device 100 shown in FIGS. 1 through 4. FIG. 5 depicts an example process 500 for operating a mobile sterilization device 100 shown in FIGS. 1 through 4 and 6.

As shown in FIG. 5, a light-emitting diode is activated (Block 502). In implementations, activating a light-emitting diode 108 can be performed using a controller 124. For example, a mobile sterilization device 100 user can cause the controller 124 to activate the light-emitting diode 108 for transmitting light via the light dispersive element 112, which can be diffused to a liquid 122, a surface 120, and/or other object.

Then, an indication of an index of refraction is received (Block 504). In implementations, receiving an index of refraction can include receiving light using a photodiode 110 with the light originating from the light-emitting diode 108 and reflected and/or refracted by a liquid 122, ambient air 128, a surface 120, and/or other object or material through the light dispersive element 112. The photodiode 110 can create a specific electrical current corresponding with an index of refraction associated with the reflected and/or refracted light from the liquid 122, the surface 120, and/or other object. The photodiode 110 can be electrically and/or communicably coupled to the controller 124. The controller 124 can then receive the specific electrical current and/or an indication of the specific electrical current and can determine the type of material using the indicated index of refraction and/or electrical current.

Next, an indication of a safety threshold is determined (Block 506). In implementations, determining an indication of a safety threshold or other threshold can be performed using controller 124 and/or processor 130. A safety threshold can include a predetermined threshold that indicates whether it is safe and/or appropriate to activate the ultraviolet light-emitting diode and transmit ultraviolet light to a liquid 122 and/or surface 120. In one specific embodiment, the controller 124 can determine that a received indication of an index of refraction indicates a liquid. In this specific embodiment, the controller 124 can then further determine that a predetermined safety threshold (e.g., to only activate the ultraviolet light-emitting diode upon receiving an indication of a specific index of refraction, such as a liquid 122) has been met. In another specific embodiment, the controller 124 can then further determine that a predetermined safety threshold (e.g., to not activate the ultraviolet light-emitting diode upon receiving an indication outside the range of a specific index of refraction) has not been met.

Then, an ultraviolet light-emitting diode is activated when a predetermined safety threshold is attained (Block 508). In an implementation, activating the ultraviolet light-emitting diode 106 when a predetermined safety threshold has been met can include using a controller 124 to activate the ultraviolet light-emitting diode 106, which can transmit ultraviolet light through the light dispersive element 112. The light dispersive element 112 can diffuse the ultraviolet light into a liquid 122 and/or onto a surface 120. The ultraviolet light then serves to sanitize the liquid 122 and/or the surface 120. Additionally, controller 124 may not activate the ultraviolet light-emitting diode 106 when it is determined that a predetermined safety threshold has not been met.

In one specific example, a user can use a sterilization assembly 102 by immersing a light dispersive element 112 into a volume of liquid 122 including water in a container 126 and activating a red light-emitting diode (LED) 108 to transmit light through and out of the light dispersive element 112. The water can then refract and reflect the LED light back through the light dispersive element 112 to a photodiode 110 disposed as part of a mobile device 104 coupled to the sterilization assembly 102, which photodiode 110 can detect the reflected LED light and output a specific electrical current in response. A controller 124 within the mobile device 104 can receive an indication of the specific electrical current and correlate the specific electrical current to the specific refractive index of water and determine that the light dispersive element 112 is disposed in water. The controller can then positively determine that a predetermined threshold has been met to only activate an ultraviolet light emitting diode 106 when the light dispersive element 112 is in a liquid and can activate the ultraviolet light emitting diode 106. The ultraviolet light emitting diode 106 can then transmit ultraviolet light through and out of the ultraviolet light emitting diode 106, which can sterilize the water.

Conclusion

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A mobile sterilization assembly, comprising:
    a sterilization assembly configured to be coupled to a mobile device having an ultraviolet light-emitting diode, the sterilization assembly including
        at least one light dispersive element comprising an optical fiber configured to diffuse ultraviolet light from the ultraviolet light-emitting diode through an end and sides of the optical fiber to sterilize a material; and
        an optical coupler configured to couple the at least one light dispersive element to the mobile device to transmit ultraviolet light from the ultraviolet light-emitting diode to the optical fiber;
    wherein the ultraviolet light-emitting diode comprises a short wave ultraviolet light-emitting diode that emits light between 250 nm and 285 nm.

2. The mobile sterilization assembly as recited in claim 1, wherein the sterilization assembly is a disposable sterilization assembly.

3. The mobile sterilization assembly as recited in claim 1, wherein at least one of the mobile device or the sterilization assembly comprises a red light-emitting diode.

4. The mobile sterilization assembly as recited in claim 1, wherein the sterilization assembly further comprises at least one visible light-emitting diode and at least one photodiode, and wherein light from the at least one visible light-emitting diode is transmitted through the optical fiber via the optical coupler to the material, and wherein light reflected from the material is transmitted through the optical fiber to the at least one photodiode.

5. The mobile sterilization assembly as recited in claim 1, wherein the at least one light dispersive element comprises cladding.

6. The mobile sterilization assembly as recited in claim 1, further comprising an ultraviolet shield configured to be disposed between the at least one light dispersive element and the mobile device.

7. A mobile sterilization assembly, comprising:
    a sterilization assembly configured to be coupled to a mobile device having an ultraviolet light-emitting diode, the sterilization assembly including
        at least one light dispersive element comprising an optical fiber configured to diffuse ultraviolet light from the ultraviolet light-emitting diode through an end and sides of the optical fiber to sterilize a material; and
        an optical coupler configured to couple the at least one light dispersive element to the mobile device to transmit ultraviolet light from the ultraviolet light-emitting diode to the optical fiber; and
    an ultraviolet shield configured to be disposed between the at least one light-dispersive element and the mobile device.

8. The mobile sterilization assembly in claim 7, wherein the sterilization assembly comprises a disposable sterilization assembly.

9. The mobile sterilization assembly in claim 7, wherein the ultraviolet light-emitting diode includes a short wave ultraviolet light-emitting diode that emits light between 250 nm and 285 nm.

10. The mobile sterilization assembly as recited in claim 7, wherein at least one of the mobile device or the sterilization assembly comprises a red light-emitting diode.

11. The mobile sterilization assembly as recited in claim 7, wherein at least one of the mobile device or the sterilization assembly comprises a red light-emitting diode, and wherein the ultraviolet light-emitting diode comprises a short wave ultraviolet light-emitting diode.

12. The mobile sterilization assembly in claim 7, wherein the sterilization assembly further comprises at least one visible light-emitting diode and at least one photodiode, wherein light from the visible light-emitting diode is transmitted through the optical fiber via the optical coupler to the material, and wherein light reflected from the material is transmitted through the optical fiber to the at least one photodiode.

13. The mobile sterilization assembly in claim 7, where the at least one light dispersive element comprises cladding.

14. A mobile sterilization assembly, comprising:
    a sterilization assembly configured to be coupled to a mobile device having an ultraviolet light-emitting diode, at least one visible light emitting diode, and at least one photodiode, the sterilization assembly including:
        at least one light dispersive element comprising an optical fiber configured to diffuse ultraviolet light from the ultraviolet light-emitting diode through an end and sides of the optical fiber to sterilize a material; and
        an optical coupler configured to couple the at least one light dispersive element to the mobile device to transmit ultraviolet light from the ultraviolet light-emitting diode to the optical fiber;
    wherein light from the visible light-emitting diode is transmitted through the optical fiber via the optical coupler to the material, and wherein light reflected from the material is transmitted through the optical fiber to the at least one photodiode.

15. The mobile sterilization assembly in claim 14, wherein the sterilization assembly comprises a disposable sterilization assembly.

16. The mobile sterilization assembly in claim 14, wherein the ultraviolet light-emitting diode includes a short wave ultraviolet light-emitting diode that emits light between 250 nm and 285 nm.

17. The mobile sterilization assembly as recited in claim 14, wherein the at least one of the mobile device or the sterilization assembly.

18. The mobile sterilization assembly in claim 14, where the at least one light dispersive element comprises cladding.

19. The mobile sterilization assembly in claim 14, further comprising an ultraviolet shield configured to be disposed between the at least one light-dispersive element and the mobile device.

20. A mobile sterilization device, comprising:
a mobile device having a controller and an ultraviolet light-emitting diode; and
a sterilization assembly configured to be coupled to the mobile device, the sterilization assembly including
at least one light dispersive element comprising an optical fiber configured to diffuse ultraviolet light from the ultraviolet light-emitting diode through an end and sides of the optical fiber to sterilize a material; and
an optical coupler configured to couple the at least one light dispersive element to the mobile device to transmit ultraviolet light from the ultraviolet light-emitting diode to the optical fiber wherein the mobile device further comprises at least one visible light-emitting diode and at least one photodiode, and wherein light from the at least one visible light-emitting diode is transmitted through the optical fiber via the optical coupler to the material, and wherein light reflected from the material is transmitted through the optical fiber to the at least one photodiode.

21. The mobile sterilization device as recited in claim 20, wherein the mobile device comprises at least one of a smartphone, a tablet computer, or a wearable computer.

22. The mobile sterilization device as recited in claim 20, wherein the sterilization assembly comprises a disposable sterilization assembly.

23. The mobile sterilization device in claim 20, wherein at least one of the mobile device or the sterilization assembly comprises a red light-emitting diode, and wherein the ultraviolet light-emitting diode comprises a short wave ultraviolet light-emitting diode.

24. The mobile sterilization device as recited in claim 20, wherein the sterilization assembly comprises at least one of the at least one light-emitting diode or the photodiode.

25. The mobile sterilization device in claim 20, wherein the sterilization assembly includes a mobile device case.

26. The mobile sterilization device as recited in claim 20, wherein the controller is configured to determine, from light received by the at least one photodiode, whether a safety parameter has been met.

27. The mobile sterilization device as recited in claim 26, wherein the safety parameter comprises a refraction index indicating a liquid.

* * * * *